(12) United States Patent
Yamamoto

(10) Patent No.: US 11,058,403 B2
(45) Date of Patent: Jul. 13, 2021

(54) ACOUSTIC WAVE DIAGNOSTIC APPARATUS AND CONTROL METHOD THEREOF

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 544 days.

(21) Appl. No.: 15/915,295

(22) Filed: Mar. 8, 2018

(65) Prior Publication Data

US 2018/0192997 A1 Jul. 12, 2018

Related U.S. Application Data

(63) Continuation of application No. PCT/JP2016/068332, filed on Jun. 21, 2016.

(30) Foreign Application Priority Data

Sep. 29, 2015 (JP) .............................. JP2015-190741

(51) Int. Cl.
*A61B 8/08* (2006.01)
*A61B 8/00* (2006.01)
*A61B 8/14* (2006.01)

(52) U.S. Cl.
CPC .............. *A61B 8/5276* (2013.01); *A61B 8/08* (2013.01); *A61B 8/145* (2013.01); *A61B 8/461* (2013.01);
(Continued)

(58) Field of Classification Search
None
See application file for complete search history.

(56) References Cited

U.S. PATENT DOCUMENTS

2008/0051659 A1* 2/2008 Waki .................. A61B 8/08 600/443
2008/0269606 A1 10/2008 Matsumura
(Continued)

FOREIGN PATENT DOCUMENTS

JP 2010-17585 A 1/2010
JP 2010-220801 A 10/2010
(Continued)

OTHER PUBLICATIONS

Extended European Search Report, dated Jun. 26, 2018, for European Application No. 16850764.8.
(Continued)

*Primary Examiner* — Bill Thomson
*Assistant Examiner* — Younhee Choi
(74) *Attorney, Agent, or Firm* — Birch, Stewart, Kolasch & Birch, LLP

(57) ABSTRACT

Using ultrasound frame data generated from the ultrasound echo reflected from the living tissue, the movement amount of the living tissue and its representative value are calculated. In a case where the representative value of the tissue movement amount is equal to or greater than a threshold value, a hue conversion LUT_large having a large degree of hue change is used, and an elastic image in which distortion is expressed by hue corresponding to the magnitude is generated. On the other hand, in a case where the representative value of the movement amount of the living tissue is less than the predetermined threshold value, a hue conversion LUT_small having a small degree of hue change is used to generate an elastic image.

3 Claims, 7 Drawing Sheets

(52) U.S. Cl.
CPC ............ *A61B 8/485* (2013.01); *A61B 8/5207* (2013.01); *A61B 8/5292* (2013.01)

(56) References Cited

U.S. PATENT DOCUMENTS

| | | | |
|---|---|---|---|
| 2009/0118615 A1* | 5/2009 | Kato | A61B 5/02007 600/438 |
| 2010/0134629 A1* | 6/2010 | Lindop | A61B 8/485 348/163 |
| 2013/0158400 A1* | 6/2013 | Inoue | A61B 8/5207 600/438 |
| 2014/0051998 A1* | 2/2014 | Shimazaki | A61B 8/485 600/438 |
| 2014/0114189 A1 | 4/2014 | Kanayama et al. | |
| 2014/0155746 A1* | 6/2014 | Tanigawa | A61B 8/485 600/438 |
| 2014/0288431 A1 | 9/2014 | Taki et al. | |

FOREIGN PATENT DOCUMENTS

| | | |
|---|---|---|
| JP | 2013-5876 A | 1/2013 |
| JP | 2013-121483 A | 6/2013 |
| JP | 2014-36778 A | 2/2014 |
| JP | 2014-42823 A | 3/2014 |
| JP | 2015-16062 A | 1/2015 |
| JP | 2015-23913 A | 2/2015 |

OTHER PUBLICATIONS

International Preliminary Report on Patentability and Written Opinion of the International Searching Authority(Forms PCT/IB/326, PCT/IB/373 and PCT/ISA/237), dated Apr. 12, 2018, for International Application No. PCT/JP2016/068332, with an English Translation of the Written Opinion.

International Search Report(Form PCT/ISA/210), dated Sep. 20, 2016, for International Application No. PCT/JP2016/068332, with English translation.

* cited by examiner

FIG. 8

| | CONVENTIONAL EXAMPLE (HUE CONVERSION LUT_large APPLIED) | THIS APPLICATION (TISSUE MOVEMENT AMOUNT LARGE: HUE CONVERSION LUT_large APPLIED) (TISSUE MOVEMENT AMOUNT SMALL: HUE CONVERSION LUT_small APPLIED) |
|---|---|---|
| TISSUE MOVEMENT AMOUNT LARGE | G, B | G, B |
| TISSUE MOVEMENT AMOUNT SMALL | B, R, R, R, R, R, R | G |

ACOUSTIC WAVE DIAGNOSTIC APPARATUS AND CONTROL METHOD THEREOF

CROSS-REFERENCE TO RELATED APPLICATIONS

This application is a Continuation of PCT International Application No. PCT/JP2016/068332 filed on Jun. 21, 2016, which claims priority under 35 U.S.C. § 119(a) to Japanese Patent Application No. 2015-190741 filed on Sep. 29, 2015. Each of the above application(s) is hereby expressly incorporated by reference, in its entirety, into the present application.

BACKGROUND OF THE INVENTION

1. Field of the Invention

The present invention relates to a diagnostic apparatus using an acoustic wave, for example, an ultrasound wave, and a control method thereof.

2. Description of the Related Art

Various diagnostic apparatuses using ultrasound waves have been developed to observe tomographic images or blood flow (JP2014-36778A, JP2013-5876A, JP2015-23913A, JP2015-16062A, JP2014-42823A, and JP2013-121483A). In recent years, elastography that measures information regarding the hardness or softness of living tissue using ultrasound waves and uses the information for medical diagnosis is also known. In elastography, an elastic image having hue (color) corresponding to the magnitude of distortion or the like indicating the hardness or softness of living tissue is used for diagnosis.

SUMMARY OF THE INVENTION

In elastography, the hardness of the living tissue is estimated by calculating the distortion of the living tissue by differentiating the movement amount (displacement) of the living tissue caused by compression, pulsation, and the like. Here, in a case where compression and pulsation are small to the extent that the displacement of the living tissue cannot be caused, it is difficult to correctly calculate the distortion of the living tissue. The distortion calculated in this case may not be the distortion of the living tissue but may be the result of erroneously recognizing the flicker of noise of the signal as distortion. That is, the distortion calculated in this case may be caused by noise. In a case where noise is erroneously recognized as distortion, the noise not caused by the hardness of the living tissue appears in the elastic image as if the noise indicates the hardness of the living tissue.

Among the above patent documents, for example, JP2014-36778A discloses displaying portions having the same elasticity in colors, which are not largely different in the elastic image, regardless of the degree of compression and relaxation of the living tissue due to heartbeat by changing the color conversion table according to the movement amount of the heart wall. However, JP2014-36778A does not take into consideration a case where the degree of compression and relaxation of the living tissue is too small to correctly calculate the distortion. For this reason, in a case where noise is erroneously recognized as a distortion because the degree of compression and relaxation of the living tissue is small, the noise is displayed in the elastic image as if the noise were normally measured as distortion.

In addition, for example, JP2013-5876A discloses that image display is performed such that a low S/N region is distinguished from a highly reliable region and the highly reliable region is set as an object to be analyzed. In JP2013-5876A, however, the low S/N region is determined from a B-mode image obtained by performing only reception processing without transmitting ultrasound waves, and the removal of noise that is erroneously recognized as distortion in a case where the movement amount of the living tissue is small has not been taken into consideration at all.

It is an object of the present invention to make noise not noticeable in an elastic image in a case where the movement amount of the living tissue is small.

An acoustic wave diagnostic apparatus according to the present invention comprises: a movement amount calculation device for generating movement amount frame data using acoustic wave frame data, which is generated using an acoustic wave echo signal indicating an acoustic wave echo reflected from a living tissue of a subject, and calculating a representative value of a movement amount using the movement amount frame data; a distortion calculation device for calculating distortion using movement amount frame data between frames; and an elastic image generation device for generating an elastic image showing the calculated distortion using a first hue conversion look-up table in a case where the calculated representative value of the movement amount is larger than a predetermined threshold value and generating an elastic image showing the calculated distortion using a second hue conversion look-up table, which has a smaller degree of hue change than the first hue conversion look-up table, in a case where the calculated representative value of the movement amount is smaller than the predetermined threshold value.

The present invention also provides a control method suitable for an acoustic wave diagnostic apparatus. That is, this method comprises: generating movement amount frame data using acoustic wave frame data, which is generated using an acoustic wave echo signal indicating an acoustic wave echo reflected from a living tissue of a subject, and calculating a representative value of a movement amount using the movement amount frame data by a movement amount calculation device; calculating distortion using movement amount frame data between frames by a distortion calculation device; and generating an elastic image showing the calculated distortion using a first hue conversion look-up table in a case where the calculated representative value of the movement amount is larger than a predetermined threshold value and generating an elastic image showing the calculated distortion using a second hue conversion look-up table, which has a smaller degree of hue change than the first hue conversion look-up table, in a case where the calculated representative value of the movement amount is smaller than the predetermined threshold value by an elastic image generation device.

In a case where the calculated representative value of the movement amount is the same as the threshold value, either the first hue conversion look-up table or the second hue conversion look-up table can be used to generate an elastic image.

In a preferable aspect, the movement amount calculation device calculates an average value of the movement amount for each unit region of a pair of pieces of acoustic wave frame data having different acquisition times, which are generated from the acoustic wave echo signal, as the representative value of the movement amount.

In an aspect, the acoustic wave diagnostic apparatus further comprises a threshold value control device for changing the threshold value according to a frame rate of acoustic wave frame data that is generated over time from the acoustic wave echo signal.

Distortion (index indicating the hardness of living tissue) expressed by hue in the elastic image is calculated from the movement amount (displacement) of the living tissue. In a case where the movement amount is small, the distortion calculated from the movement amount is easily influenced by noise. According to the present invention, in a case where the representative value of the movement amount is smaller than the predetermined threshold value, an elastic image is generated by using the second hue conversion look-up table having a smaller degree of hue change than the first hue conversion look-up table that is used in a case where the representative value of the movement amount is larger than the threshold value. Therefore, in a case where the movement amount is small, it is possible to prevent noise from appearing noticeably in the elastic image due to the hue or to reduce the noise.

BRIEF DESCRIPTION OF THE DRAWINGS

FIG. 8 shows an elastic image in the conventional technique and an elastic image in the ultrasound diagnostic apparatus of the present application for each of a case where the tissue movement amount is large and a case where the tissue movement amount is small.

DESCRIPTION OF THE PREFERRED EMBODIMENTS

In an embodiment described below, an example using an ultrasound wave as an acoustic wave will be described. Without being limited to the ultrasound wave, an acoustic wave having an audible frequency may also be used as long as an appropriate frequency is selected according to an object to be examined, measurement conditions, and the like.

Figure 1:
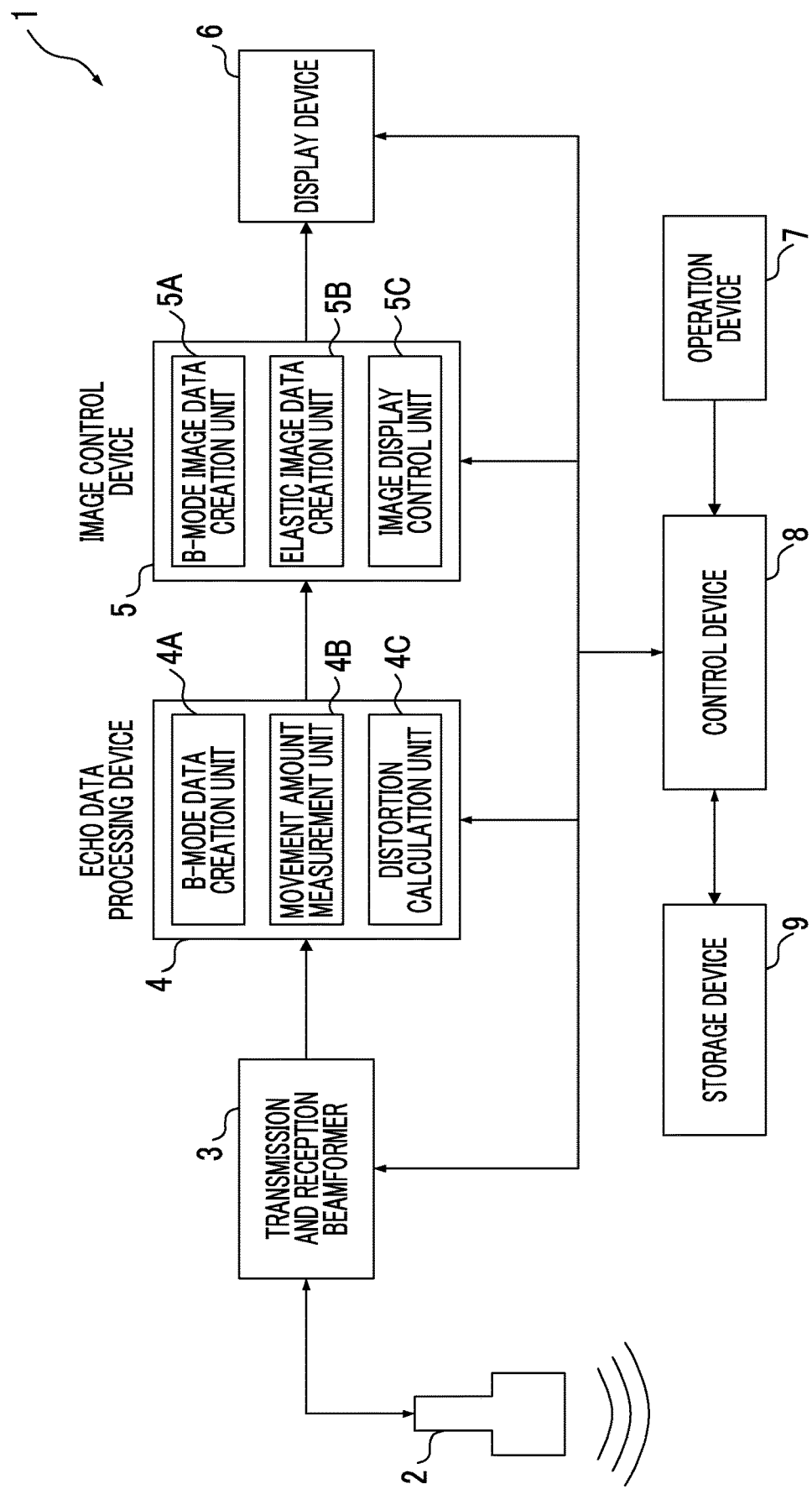
FIG. 1 is a block diagram showing the overall configuration of an ultrasound diagnostic apparatus.

FIG. 1 shows a block diagram showing the overall configuration of an ultrasound diagnostic apparatus 1. The ultrasound diagnostic apparatus 1 includes an ultrasound probe 2, a transmission and reception beamformer 3, an echo data processing device 4, an image control device 5, a display device 6, an operation device 7, a control device 8, and a storage device 9.

The overall operation of the ultrasound diagnostic apparatus 1 is controlled by the control device 8. A control program for controlling various devices to be described in detail below, which form the ultrasound diagnostic apparatus 1, a hue conversion look-up table to be described later, frame data, and the like are stored in the storage device 9 connected to the control device 8. An instruction from the operator, a value to be set or adjusted, and the like are input from the operation device 7.

The ultrasound probe 2 is pressed against the body surface of the subject (patient). The ultrasound probe 2 transmits an ultrasound beam toward the subject and receives an ultrasound echo reflected from the living tissue in the subject, and outputs an ultrasound echo signal indicating an ultrasound echo. The ultrasound probe 2 having an arbitrary shape, such as a convex type, a sector type, and a linear type, can be used.

The transmission and reception beamformer 3 performs a scanning using an ultrasound beam by driving the ultrasound probe 2 under predetermined scanning conditions. Any scanning method, such as sector scanning, offset sector scanning, and linear scanning, can be adopted. In addition, the transmission and reception beamformer 3 performs predetermined signal processing, such as phasing addition processing, on the ultrasound echo signal from the ultrasound probe 2, and generates ultrasound frame data (tomographic echo data) corresponding to one scanning plane (one tomographic plane) of living tissue. The generated ultrasound frame data is sequentially stored in the storage device 9. The ultrasound frame data is generated over time according to a predetermined frame rate (the number of pieces of ultrasound frame data generated per unit time). By changing the transmission timing of the ultrasound beam transmitted by the ultrasound probe 2, the frame rate of the ultrasound frame data can be changed.

The ultrasound frame data is then input to the echo data processing device 4. The echo data processing device 4 includes a B-mode data creation unit 4A, a movement amount measurement unit 4B, and a distortion calculation unit 4C.

The B-mode data creation unit 4A creates B-mode data by performing logarithmic compression processing, envelope detection processing, and the like on the ultrasound frame data.

The movement amount measurement unit 4B (movement amount calculation device) calculates the following movement amount using the ultrasound frame data. That is, the movement amount frame data is created by calculating the movement amount of the living tissue for each unit region (for each pixel) based on a pair of pieces of frame data at predetermined time intervals among a plurality of pieces of ultrasound frame data having different acquisition times sequentially stored in the storage device 9. The unit of the movement amount can be a pixel (pix). Thereafter, a representative value of the tissue movement amount is calculated by calculating the average value of the movement amount for each unit region in the movement amount frame data. As will be described later, the calculated representative value of the tissue movement amount is used for the setting (selection and switching) of a hue conversion look-up table. The representative value of the tissue movement amount may be calculated using a unit region at the frame center instead of the entire frame, and a maximum value, a minimum value, a variance, and the like may be used as the representative value of the tissue movement amount instead of an average value. In a case where a part of the ultrasound image is designated as a region of interest (ROI), the representative value of the tissue movement amount may be calculated using the unit region in the ROI.

The distortion calculation unit 4C (distortion calculation device) calculates a distortion for each unit region (each pixel) based on the movement amount frame data created by the movement amount measurement unit 4B described above, thereby creating distortion frame data. The distortion frame data is created (calculated) by differentiating the movement amount frame data.

The B-mode data output from the B-mode data creation unit 4A of the echo data processing device 4 and the distortion frame data output from the distortion calculation unit 4C are input to the image control device 5. The image control device 5 includes a B-mode image data creation unit 5A, an elastic image data creation unit 5B, and an image display control unit 5C.

The B-mode image data creation unit 5A creates two-dimensional tomographic image data (B-mode image data) suitable for display on the display device 6 by performing scan conversion on the B-mode data using a scan converter. In the B-mode image data, the signal strength is expressed by brightness. For example, the B-mode image data has information indicating the brightness of 256 gradations for each pixel.

The elastic image data creation unit 5B creates color elastic image data indicating distortion for each unit region in the distortion frame data with a hue (difference in color) corresponding to the magnitude of the distortion, that is, performs processing for coloring of distortion. In the elastic image expressed by the elastic image data, the magnitude of distortion is expressed by the difference in color. The correspondence relationship between the magnitude of distortion and the hue is based on the hue conversion look-up table stored in advance in the storage device 9. Details of the hue conversion look-up table will be described later.

The image display control unit 5C combines the B-mode image data and the elastic image data to create composite image data. The composite image data is transmitted to the display device 6, so that a composite ultrasound image in which the B-mode image and the elastic image are combined is displayed on the display screen of the display device 6. Needless to say, instead of combining the B-mode image and the elastic image, the B-mode image and the elastic image may be displayed side by side on the display screen.

Figure 2:
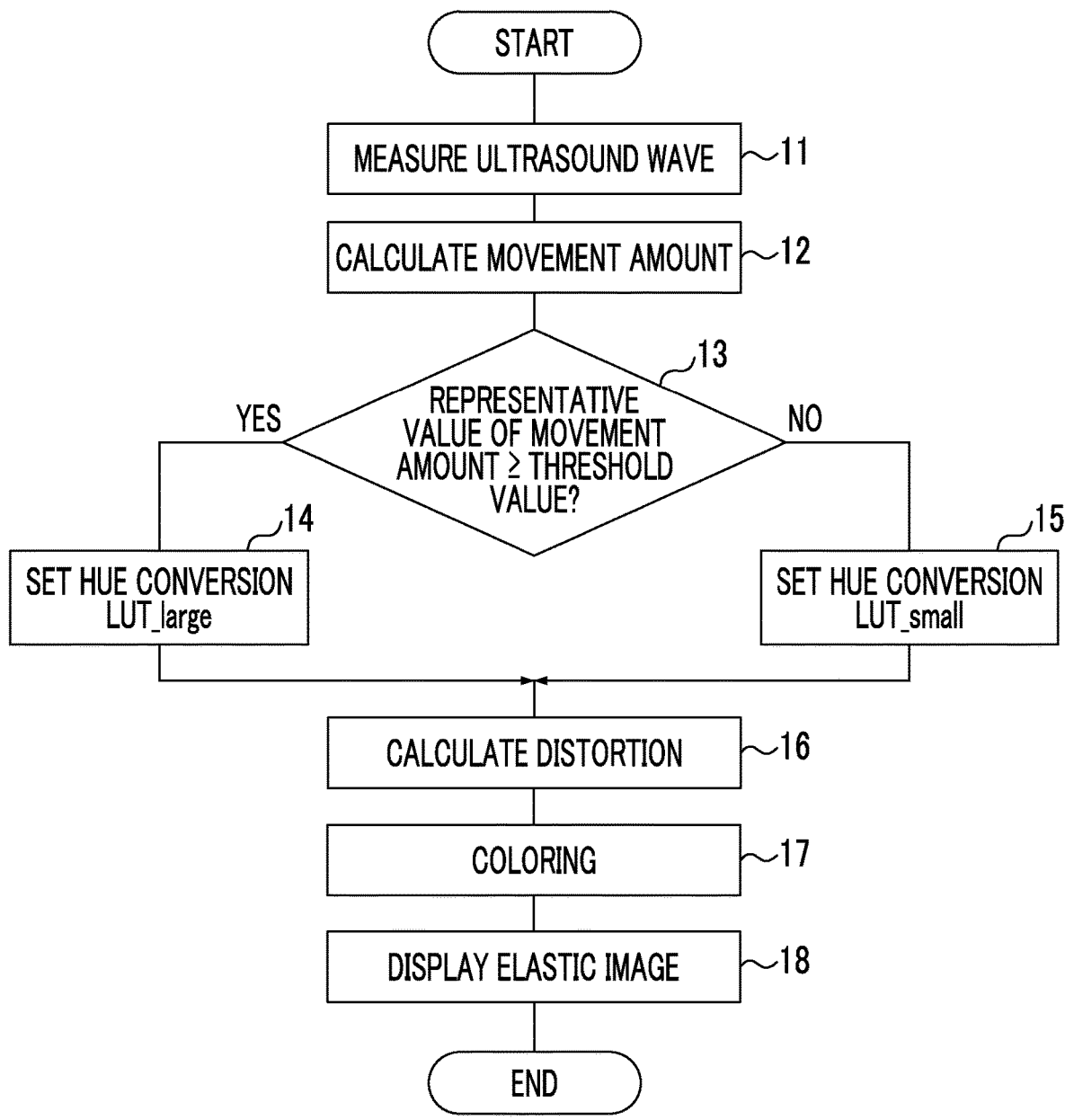
FIG. 2 is a flowchart showing the flow of the process for creating an elastic image.

FIG. 2 is a flowchart showing the process of creating an elastic image in the ultrasound diagnostic apparatus 1.

Ultrasound frame data corresponding to the tomographic plane (one scanning plane) is continuously acquired while physically displacing the living tissue by lightly pressing the ultrasound probe 2 against the subject or by using the pulsation of the heart or the like (measurement of ultrasound waves) (step 11). The ultrasound frame data is acquired at a predetermined frame rate, and is sequentially recorded in the storage device 9.

By using a pair of pieces of ultrasound frame data among the pieces of ultrasound frame data sequentially recorded in the storage device 9, the echo data processing device 4 measures the movement amount of the tissue for each unit region of the ultrasound frame data, thereby creating movement amount frame data. Then, the representative value of the tissue movement amount described above is calculated (step 12).

Then, corresponding to the magnitude of the calculated representative value of the tissue movement amount, a hue conversion look-up table (hereinafter, referred to as a hue conversion LUT) is set (steps 13, 14, and 15).

Figure 3:
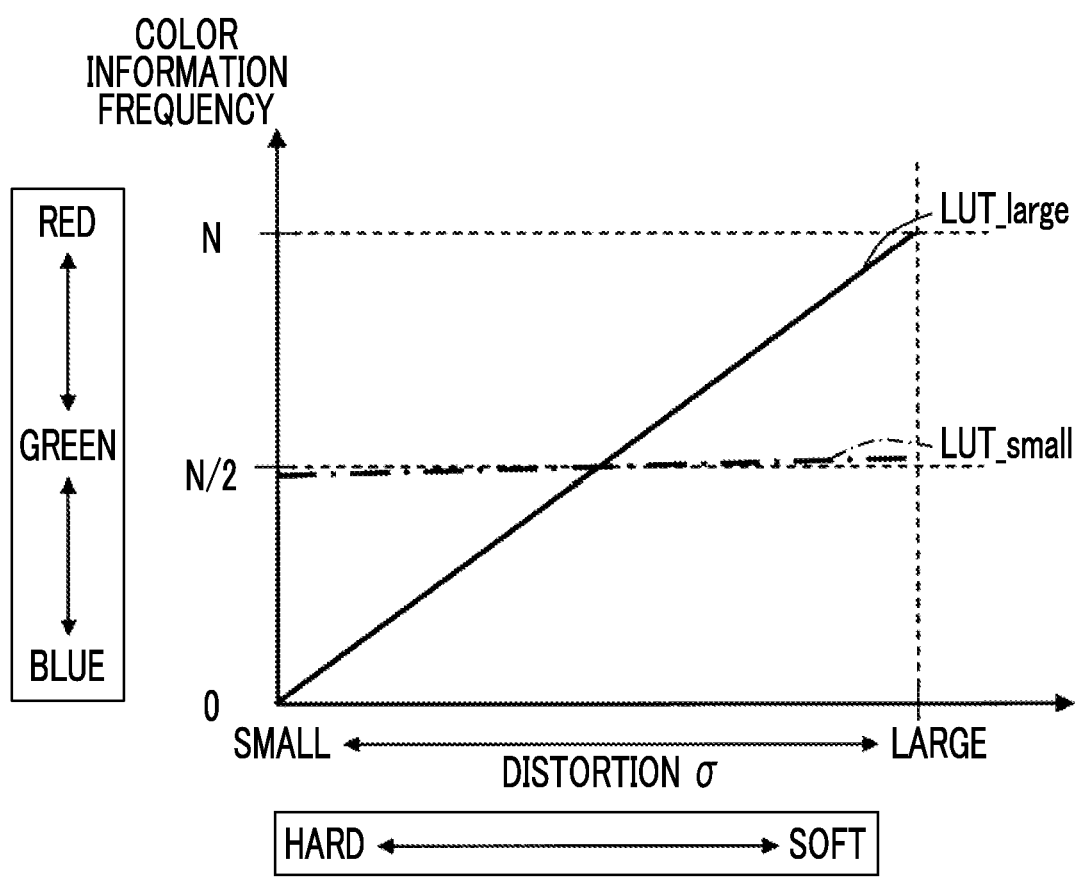
FIG. 3 shows a hue conversion look-up table.

FIG. 3 shows the hue conversion LUTs stored in the storage device 9 in a graph with a distortion a on the horizontal axis and a color information frequency N on the vertical axis. The color information frequency N takes a value between 0 to 255.

The hue conversion LUT is used to convert the distortion into a hue corresponding to the magnitude. A living tissue with large distortion (soft living tissue) is generally associated with red. Conversely, a living tissue with small distortion (hard living tissue) is generally associated with blue. Green is associated with distortion of intermediate magnitude. As a result, the hardness of the living tissue is visualized in an easy-to-understand manner according to the hue.

Two hue conversion LUTs of a hue conversion LUT large and a hue conversion LUT small are stored in the storage device 9. Referring to FIG. 3, the gradient of the graph (solid line) of the hue conversion LUT large (the ratio of the degree of hue change to the amount of change in distortion, the inclination of the graph) is large, while the gradient of the graph (one-dot chain line) of the hue conversion LUT_small is very small. The hue conversion LUT_large with a large gradient device that the degree of hue change with respect to the amount of change in distortion is large and the color expression range is wide. On the other hand, the hue conversion LUT small with a small gradient device that the degree of hue change with respect to the amount of change in distortion is small and the color expression range is narrow. The graph of the hue conversion LUT_large and the graph of the hue conversion LUT_small intersect at N/2 (green).

Returning to FIG. 2, one of the hue conversion LUT large and the hue conversion LUT small is selected according to the magnitude of the representative value of the tissue movement amount calculated in the echo data processing device 4. The control device 8 compares the representative value of the tissue movement amount with a predetermined threshold value (step 13). In a case where the representative value is equal to or greater than the predetermined threshold value, the hue conversion LUT_large is set (YES in step 13, step 14). That is, the hue conversion LUT_large is read from the storage device 9 to be transmitted to the image control device 5. On the other hand, in a case where the representative value is less than the predetermined threshold value, the hue conversion LUT_small is set (NO in step 13, step 15). Needless to say, the hue conversion LUT large may be set in a case where the representative value exceeds the predetermined threshold value, and the hue conversion LUT_small may be set in a case where the representative value is equal to or less than the predetermined threshold value.

In a case where the representative value of the tissue movement amount is equal to or greater than the threshold value, it is thought that the tissue movement amount is caused by the hardness of the living tissue. Therefore, the reliability is high. In this case, an elastic image (elastographic image) that is not different from the conventional one can be expressed by using the hue conversion LUT_large having a conventional gradient. On the other hand, in a case where the representative value of the tissue movement amount is smaller than the threshold value, the tissue movement amount may be dominated by noise rather than being caused by the hardness of the living tissue. In this case, by using the hue conversion LUT_small with a small gradient, it is possible to obtain an elastic image with no noticeable noise (details will be described later).

By differentiating the movement amount frame data in the echo data processing device 4, the distortion for each unit region is calculated, and distortion frame data is created (step 16). Then, by performing hue conversion of the distortion frame data using the hue conversion LUT_large or the hue conversion LUT_small described above so that coloring is realized, elastic image data is created (step 17). An elastic image with distortion expressed by hue corresponding to its magnitude is displayed on the display device 6 under the control of the image control device 5 (step 18).

Figure 4:
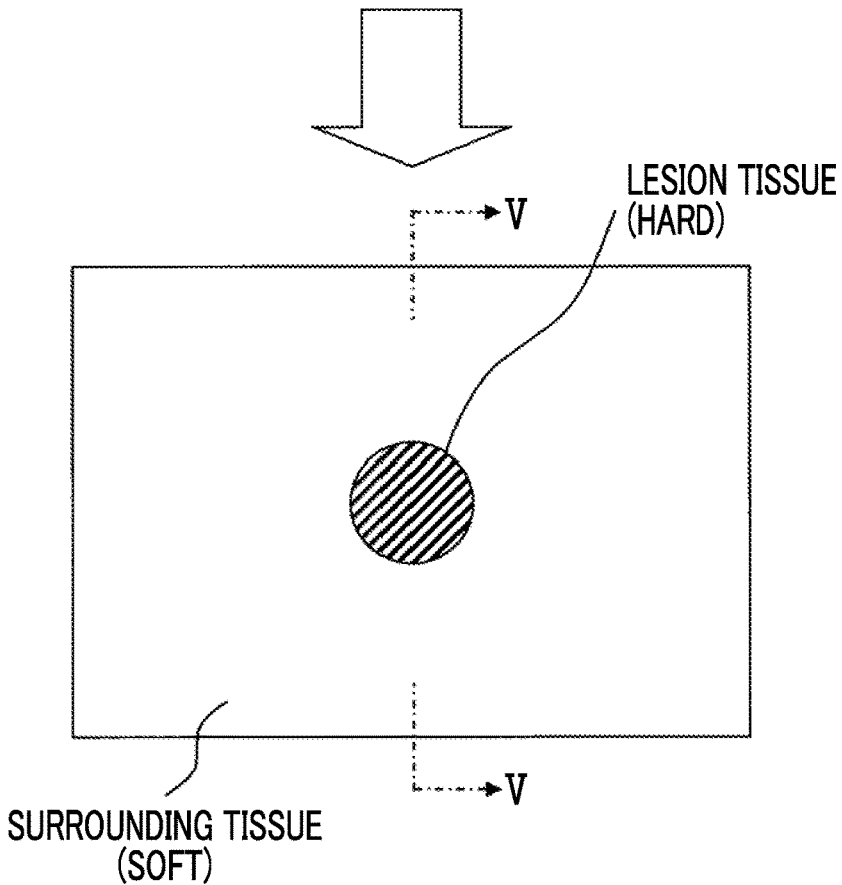
FIG. 4 schematically shows the inside of the living body in which a lesion tissue is present.
Figure 5:
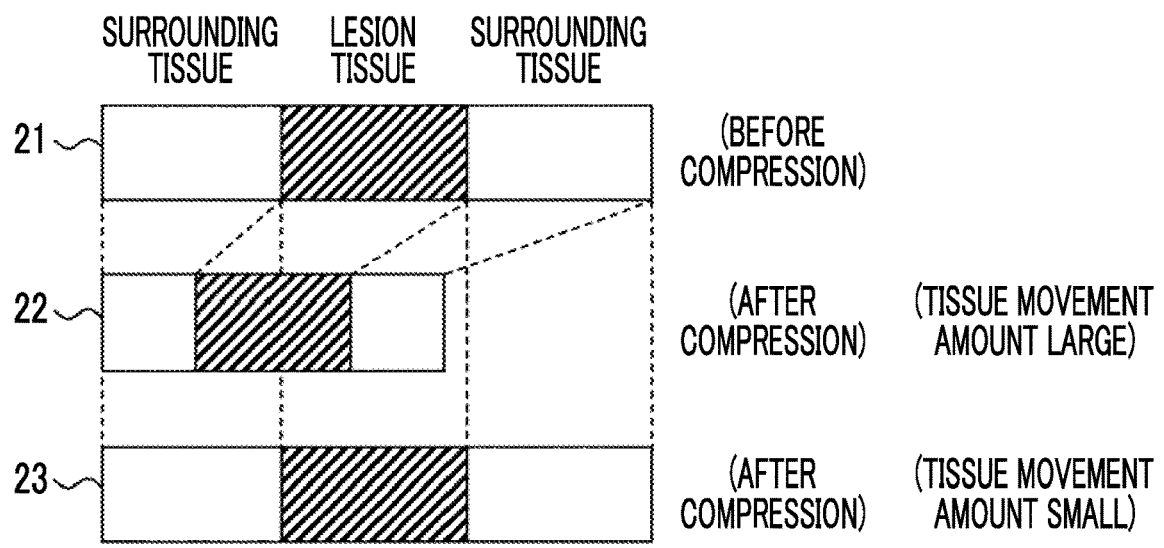
FIG. 5 shows the positions of the surrounding tissue and the lesion tissue before compression, the positions of the surrounding tissue and the lesion tissue after compression in a case where the tissue movement amount is large, and the positions of the surrounding tissue and the lesion tissue after compression in a case where the tissue movement amount is small.

Referring to FIGS. 4 to 8, an effect of selecting either the hue conversion LUT large or the hue conversion LUT_small according to the tissue movement amount will be described. FIG. 4 schematically shows the inside of a living body in which a hard lesion tissue is present so as to be surrounded by a soft surrounding tissue (normal living tissue). FIG. 5 schematically shows a surrounding tissue and a lesion tissue along the line V-V of FIG. 4, that is, at the cross-sectional position passing through the lesion tissue. Reference numeral 21 indicates a surrounding tissue and a lesion tissue before compression (during relaxation), and reference numerals 22 and 23 indicate a surrounding tissue and a lesion tissue after compression (during compression). Here, reference numeral 22 schematically shows a case where the tissue movement amount is large, and reference numeral 23 schematically shows a case where the tissue movement amount is small. For the sake of clarity, in the schematic diagram of the surrounding tissue and the lesion tissue denoted by reference numerals 21 to 23 in FIG. 5, the left end of the surrounding tissue is shown as a fixed end (no displacement).

Figure 6:
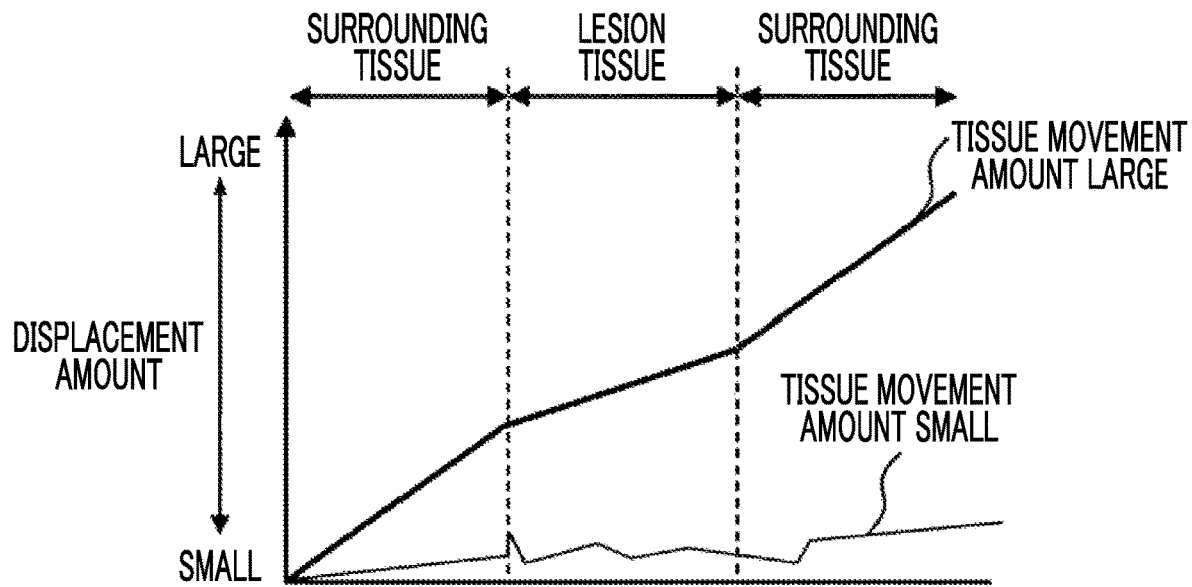
FIG. 6 is a graph showing the amount of displacement of the surrounding tissue and the lesion tissue before and after compression.
Figure 7:
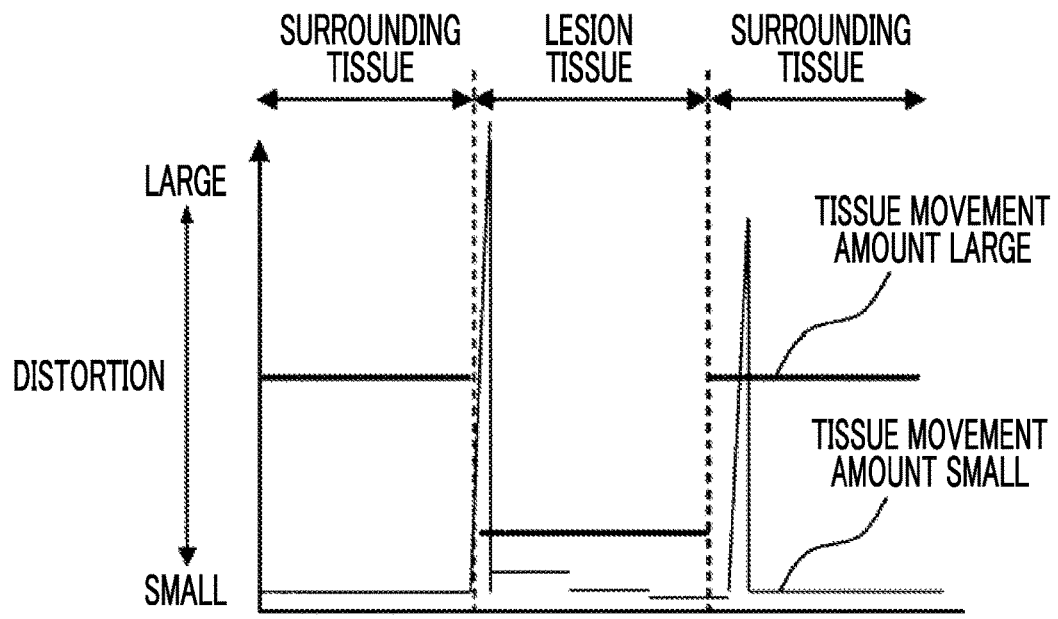
FIG. 7 is a graph showing distortion of the surrounding tissue and the lesion tissue.

FIG. 6 shows the amount of displacement of the surrounding tissue and the lesion tissue before and after compression denoted by reference numerals 21 and 22 and reference numerals 21 and 23 in FIG. 5. FIG. 7 shows the differentiation of the displacement shown in FIG. 6. In FIGS. 6 and 7, the graph (relationship between reference numerals 21 and 22 in FIG. 5) in a case where the tissue movement amount is large (representative value is equal to or greater than the threshold value) is shown by a thick solid line, and the graph (relationship between reference numerals 21 and 23 in FIG. 5) in a case where the tissue movement amount is small (representative value is less than the threshold value) is shown by a thin solid line.

FIG. 8 shows a conventional elastic image, in which only the hue conversion LUT_large is used, and an elastic image displayed in the ultrasound diagnostic apparatus 1 of the present application, in which the hue conversion LUT_large is set in a case where the tissue movement amount is large and the hue conversion LUT_small is set in a case where the tissue movement amount is small, side by side for each of the case where the tissue movement amount is large and the case where the tissue movement amount is small. In the elastic image shown in FIG. 8, the tissue range displayed in blue is schematically indicated by "B", the tissue range displayed in red is schematically indicated by "R", and the tissue range displayed in green is schematically indicated by "G".

First, a case where the tissue movement amount is large, that is, a case where the representative value of the tissue movement amount is equal to or greater than the threshold value, will be described. Referring to the relationship between reference numerals 21 and 22 in FIG. 5 and the thick solid line graph in FIG. 6, in a case where the tissue movement amount is large, there is a large difference between the amount of displacement of the soft surrounding tissue and the amount of displacement of the hard lesion tissue (inclinations of the graphs are completely different). With reference to the thick solid line in FIG. 7, in a case where the tissue movement amount is large, a large value is calculated for the soft surrounding tissue and a small value is calculated for the hard lesion tissue as the distortion calculated by differentiating the displacement (differentiating the displacement in the depth direction). Referring to FIG. 8, in a case where the tissue movement amount is large, the hue conversion LUT_large is used in both a conventional example and the present application. In the elastic image, the lesion tissue is expressed in blue B indicating "hard" (small distortion). The surrounding tissue is expressed in a color (here, green G) indicating "softer than the lesion tissue". It is possible to visually recognize the presence of a hard living tissue (lesion tissue).

Next, a case where the tissue movement amount is small, that is, a case where the representative value of the tissue movement amount is less than the threshold value, will be described. In the case of displacing the living tissue by compression of the ultrasound probe, the tissue movement amount is small in a case where the compression of the ultrasound probe is very small or in a case where the measurement place of the subject is deep (distance from the ultrasound probe is large). In the case of displacing the living tissue by pulsation, the tissue movement amount is small in a case where the measurement place of the subject is far from the heart or the aorta and the pulsation is difficult to be transmitted.

Referring to the relationship between reference numerals 21 and 23 in FIG. 5 and the thin line in FIG. 6, in a case where the tissue movement amount is small, no difference in displacement between the amount of displacement of the surrounding tissue and the amount of displacement of the lesion tissue may be observed, and a noise signal may appear. In a case where this is differentiated, referring to the thin line graph in FIG. 7, a large value (noise) that is not caused by the difference between the hardness of the lesion tissue and the hardness of the surrounding tissue is calculated as large distortion.

Referring to FIG. 8, in the conventional technique in which the same hue conversion LUT_large is used regardless of the magnitude of the tissue movement amount, in a case where the tissue movement amount is small, a hue (in this case, red (R): color indicating "soft") due to noise that does not indicate the hardness of the living tissue appears in the elastic image. On the other hand, in the present application in which the hue conversion LUT_small is used in a case where the representative value of the tissue movement amount is smaller than the threshold value, the color expression range of the hue conversion LUT_small is narrow (FIG. 3). Therefore, the hue based on the noise that is not caused by the hardness of the living tissue is not displayed noticeably in the elastic image. In this manner, in a case where the tissue movement amount is small, it is possible to prevent an elastic image with noticeable noise from being displayed.

It is desirable to set the above-described threshold value, for example, between 0.2 and 0.5 pixel. This value is a variation range in a case where the flicker of noise is calculated as the amount of displacement. Since the flicker of noise varies depending on the performance of a system, a probe, and the like that are used, it is desirable to set an appropriate threshold value by checking to what degree of displacement amount the flicker of noise corresponds for each condition to be used.

Figure 9:
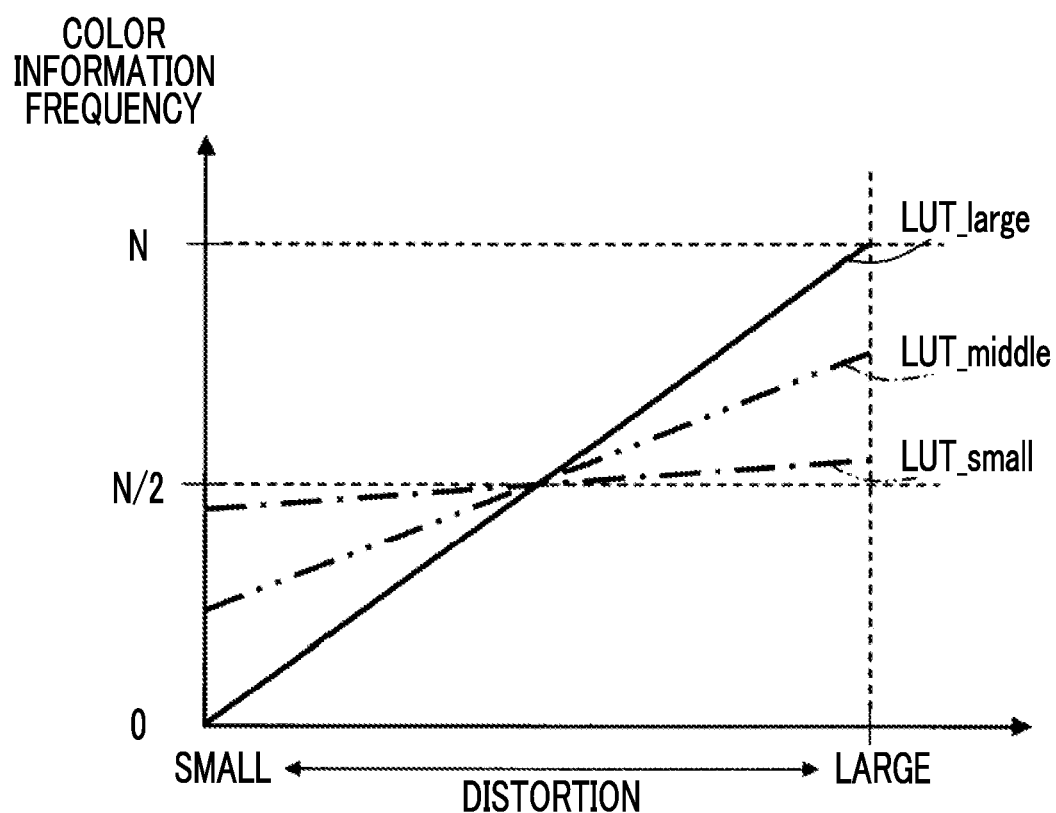
FIG. 9 shows another example of the hue conversion look-up table.

FIG. 9 shows another example of the hue conversion LUTs stored in the storage device 9. In addition to the hue conversion LUT_large and the hue conversion LUT_small, a hue conversion LUT_middle having an intermediate color expression range is stored.

For example, the hue conversion LUT_small (one-dot chain line) with the smallest inclination of the graph is set in a case where the representative value of the calculated tissue movement amount is less than 0.5 pixel, the hue conversion LUT_middle (two-dot chain line) with the inclination of the intermediate graph is set in a case where the representative value of the calculated tissue movement amount is equal to or greater than 0.5 pixel and less than 1 pixel, and the hue conversion LUT_large (solid line) is set in a case where the representative value of the calculated tissue movement amount is 1 pixel or more.

Four or more hue conversion LUTs having different color expression ranges may be stored in the storage device 9, and the hue conversion LUT to be set may be finely switched according to the magnitude of the representative value of the calculated tissue movement amount. Needless to say, the hue conversion LUT may be set more finely by defining the hue conversion LUT as a function of the representative value of the tissue movement amount. The hue may be a color display based on gray scale. In this case, an elastic image is displayed by a change in gradation from white to black.

The above-described threshold value for switching the hue conversion LUT may be changed according to the frame rate of the ultrasound diagnostic apparatus 1. For example, in a case where the frame rate is doubled, the tissue movement amount calculated by a pair of frames is halved. Assuming that a threshold value at a certain frame rate is A, it is possible to prevent the change of the frame rate from affecting the switching of the hue conversion LUT by setting the threshold value to A/2 in a case where the frame rate is doubled. For example, the threshold may be set between 0.1 pixel and 0.5 pixel in a case where the frame rate is equal to or higher than 20 fr/sec, and the threshold may be set between 0.2 pixel and 1.0 pixel in a case where the frame rate is less than 20 fr/sec. The change of the frame rate can be input from the operation device 7, and the change of the threshold value according to the frame rate can be executed with the control device 8.

What is claimed is:

1. An acoustic wave diagnostic apparatus comprising, a processing device configured to:
   generate movement amount frame data using acoustic wave frame data, which is generated using an acoustic wave echo signal indicating an acoustic wave echo reflected from a living tissue of a subject;
   calculate a representative value of a movement amount using the movement amount frame data;
   calculate distortion using the movement amount frame data between frames;
   generate an elastic image showing the calculated distortion using a first hue conversion look-up table when the calculated representative value of the movement amount is larger than a threshold value; and
   generate an elastic image showing the calculated distortion using a second hue conversion look-up table, which has a smaller degree of hue change than the first hue conversion look-up table, when the calculated representative value of the movement amount is smaller than the threshold value,
   wherein the processing device is further configured to change the threshold value according to a frame rate of acoustic wave frame data that is generated over time from the acoustic wave echo signal.

2. The acoustic wave diagnostic apparatus according to claim 1,
   wherein the processing device is further configured to calculate an average value of the movement amount for each unit region of a pair of pieces of acoustic wave frame data having different acquisition times, which are generated from the acoustic wave echo signal, as the representative value of the movement amount.

3. A control method of an acoustic wave diagnostic apparatus, wherein the control method comprising:
   generating, by the acoustic wave diagnostic apparatus, movement amount frame data using acoustic wave frame data, which is generated using an acoustic wave echo signal indicating an acoustic wave echo reflected from a living tissue of a subject;
   calculating a representative value of a movement amount using the movement amount frame data by a movement amount calculation device of the acoustic wave diagnostic apparatus;
   calculating distortion using the movement amount frame data between frames by a distortion calculation device of the acoustic wave diagnostic apparatus;
   generating, by the acoustic wave diagnostic apparatus, an elastic image showing the calculated distortion using a first hue conversion look-up table when the calculated representative value of the movement amount is larger than a threshold value;
   generating, by the acoustic wave diagnostic apparatus, an elastic image showing the calculated distortion using a second hue conversion look-up table, which has a smaller degree of hue change than the first hue conversion look-up table, when the calculated representative value of the movement amount is smaller than the threshold value by an elastic image generation device; and
   changing, by the acoustic wave diagnostic apparatus, the threshold value according to a frame rate of acoustic wave frame data that is generated over time from the acoustic wave echo signal.

* * * * *